(12) United States Patent
Chackerian et al.

(10) Patent No.: US 12,161,710 B2
(45) Date of Patent: Dec. 10, 2024

(54) MALARIA IMMUNOGEN AND METHODS FOR USING SAME

(71) Applicants: Bryce Chackerian, Albuquerque, NM (US); David S. Peabody, Albuquerque, NM (US); Lucia Jelinkova, Albuquerque, NM (US); UNM RAINFOREST INNOVATIONS, Albuquerque, NM (US); THE JOHNS HOPKINS UNIVERSITY, Baltimore, MD (US); VAXINE PTY LTD., Bedford Park (AU)

(72) Inventors: Bryce Chackerian, Albuquerque, NM (US); David S. Peabody, Albuquerque, NM (US); Nikolai Petrovsky, Bedford Park (AU); Lucia Jelinkova, Albuquerque, NM (US); Fidel Zavala, Baltimore, MD (US)

(73) Assignees: UNM RAINFOREST INNOVATIONS, Albuquerque, NM (US); THE JOHNS HOPKINS UNIVERSITY, Baltimore, MD (US); VAXINE PTY LTD., Bedford Park (AU)

( * ) Notice: Subject to any disclaimer, the term of this patent is extended or adjusted under 35 U.S.C. 154(b) by 445 days.

(21) Appl. No.: 17/628,640

(22) PCT Filed: Jul. 24, 2020

(86) PCT No.: PCT/US2020/043375
§ 371 (c)(1),
(2) Date: Jan. 20, 2022

(87) PCT Pub. No.: WO2021/016509
PCT Pub. Date: Jan. 28, 2021

(65) Prior Publication Data
US 2022/0280632 A1   Sep. 8, 2022

Related U.S. Application Data

(60) Provisional application No. 62/878,003, filed on Jul. 24, 2019.

(51) Int. Cl.
*A61K 39/02* (2006.01)
*A61K 39/12* (2006.01)
*A61P 33/06* (2006.01)
*C07K 14/005* (2006.01)
*C12N 7/00* (2006.01)
*A61K 38/00* (2006.01)

(52) U.S. Cl.
CPC .............. *A61K 39/12* (2013.01); *A61P 33/06* (2018.01); *C07K 14/005* (2013.01); *C12N 7/00* (2013.01); *A61K 38/00* (2013.01)

(58) Field of Classification Search
None
See application file for complete search history.

(56) References Cited

U.S. PATENT DOCUMENTS

| 4,722,840 | A | 2/1988 | Valenzuela et al. |
| 5,234,809 | A | 8/1993 | Boom et al. |
| 7,776,616 | B2 | 8/2010 | Heath et al. |
| 7,957,913 | B2 | 6/2011 | Chinitz et al. |
| 9,012,208 | B2 | 4/2015 | Selden et al. |

FOREIGN PATENT DOCUMENTS

| EP | 0421635 B1 | 7/1995 |
| WO | 0032227 A2 | 6/2000 |
| WO | 02056905 A2 | 7/2002 |
| WO | 03024481 A2 | 3/2003 |
| WO | 03092714 A2 | 11/2003 |
| WO | 2004007538 A2 | 1/2004 |
| WO | 2018148660 A1 | 8/2018 |
| WO | 2018193063 A2 | 10/2018 |
| WO | 2021016509 A1 | 1/2021 |

OTHER PUBLICATIONS

Anker et al., "$V_H$ and $V_L$ region structure of antibodies that recognize the $(NANP)_3$ dodecapeptide sequence in the circumsporozoite protein of Plasmodium falciparum," Dec. 1990, *European Journal of Immunology*, 20(12):2757-2761.

Espinosa et al., "Development and Assessment of Transgenic Rodent Parasites for the Preclinical Evaluation of Malaria Vaccines," 2016, *Methods in Molecular Biology*, 1403:583-601.

Green et al., *Molecular Cloning: A Laboratory Manual*, Fourth Edition, Cold Spring Harbor Laboratory Press, Woodbury, NY, 2012, Cover page, title page and table of contents.

Aida et al., "Removal of endotoxin from protein solutions by phase separation using Triton X-114," Journal of immunological Methods, Sep. 14, 1990, vol. 132, No. 2, pp. 191-195.

Atcheson et al., "A VLP for validation of the Plasmodium falciparum circumsporozoite protein junctional epitope for vaccine development," npj Vaccines, Apr. 1, 2021, vol. 6, No. 46, pp. 1-9.

Calvo-Calle et al., "Identification of a neutralizing epitope within minor repeat region of Plasmodium falciparum CS protein," npj Vaccines, Jan. 18, 2021, vol. 6, No. 10, pp. 1-8.

Fialova et al., "Comparison of different enzyme-linked immunosorbent assay methods for avidity determination of antiphospholipid antibodies," Journal of Clinical Laboratory Analysis, Nov. 2017, vol. 31, No. 6, pp. 1-9.

(Continued)

Primary Examiner — Jennifer E Graser
(74) Attorney, Agent, or Firm — MUETING RAASCH GROUP

(57) ABSTRACT

An immunogen useful for treating malaria generally includes an immunogenic carrier and an antigenic malaria circumsporozoite protein (CSP) peptide that includes the peptide NPDPNANPNVDPNAN (amino acids 5-19 of SEQ ID NO:1) linked to the immunogenic carrier. The immunogen may be administered to a subject having or at risk of having malaria.

12 Claims, 10 Drawing Sheets

Specification includes a Sequence Listing.

(56) References Cited

OTHER PUBLICATIONS

Flores-Garcia et al., "Optimization of an in vivo model to study immunity to Plasmodium falciparum pre-erythrocytic stages," Malaria Journal, Dec. 2019, vol. 18, pp. 1-9.
Francica et al., "Design of alphavirus virus-like particles presenting circumsporozoite junctional epitopes that elicit protection against malaria," Vaccines, Mar. 18, 2021, vol. 9, No. 272, pp. 1-15.
International Preliminary Report on Patentability for PCT/US2020/043375, issued Jan. 25, 2022, 8 pages.
International Search Report and Written Opinion for PCT/US2020/043375, issued Oct. 8, 2020, 11 pages.
Jelinkova et al., "A vaccine targeting the L9 epitope of the malaria circumsporozoite protein confers protection from blood-stage infection in a mouse challenge model," npj Vaccines, 2022, vol. 34, pp. 1-4.
Jelinkova et al., "An epitope-based malaria vaccine targeting the junctional region of circumsporozoite protein," npj Vaccines, 2021, vol. 6, No. 13, pp. 1-10.
Kisalu et al., "A human monoclonal antibody prevents malaria infection and defines a new site of vulnerability on Plasmodium falciparum circumsporozoite protein," Nature Medicine, May 2018, vol. 24, pp. 408-416.
Kozlovska et al., "RNA phage Qβ coat protein as a carrier for foreign epitopes," Intervirology, 1996, vol. 39, No. 1-2, pp. 9-15.
Noe et al., "A full-length Plasmodium falciparum recombinant circumsporozoite protein expressed by Pseudomonas fluorescens platform as a malaria vaccine candidate," PloS One, Sep. 23, 2014, vol. 9, No. 9, pp. 1-15.
Olotu et al., "Seven-year efficacy of RTS, S/AS01 malaria vaccine among young African children," New England Journal of Medicine, Jun. 30, 2016, vol. 374, No. 26, pp. 2519-2529.
Oyen et al., "Structure and mechanism of monoclonal antibody binding to the junctional epitope of Plasmodium falciparum circumsporozoite protein," PLoS Pathogens, Mar. 9, 2020, vol. 16, No. 3, pp. 1-22.
Penny et al., "The time-course of protection of the RTS, S vaccine against malaria infections and clinical disease," Malaria Journal, 2015, vol. 14, No. 437, pp. 1-13.
Petrovsky et al., "Advax™, a novel microcrystalline polysaccharide particle engineered from delta inulin, provides robust adjuvant potency together with tolerability and safety," Vaccine, Nov. 4, 2015, vol. 33, No. 44, pp. 5920-5926.
RTS,S Clinical Trials Partnership, "Efficacy and safety of RTS, S/AS01 malaria vaccine with or without a booster dose in infants and children in Africa: final results of a phase 3, individually randomised, controlled trial," Lancet, Jul. 4, 2015, vol. 386, No. 9988, pp. 31-45.
Schneider et al., "NIH Image to ImageJ: 25 years of image analysis," Nature Methods, Jul. 2012, vol. 9, No. 7, pp. 671-675.
Smiley et al., "Enhanced readthrough of opal (UGA) stop codons and production of Mycoplasma pneumoniae P1 epitopes in *Escherichia coli*," Gene, Nov. 30, 1993, vol. 134, No. 1, pp. 33-40.
Stoute et al., "A preliminary evaluation of a recombinant circumsporozoite protein vaccine against Plasmodium falciparum malaria," New England Journal of Medicine, Jan. 9, 1997, vol. 336, No. 2, pp. 86-91.
Tan et al., "A public antibody lineage that potently inhibits malaria infection through dual binding to the circumsporozoite protein," Nature Medicine, May 2018, vol. 24, No. 4, pp. 401-407.
Tatusova et al., "BLAST 2 Sequences, a new tool for comparing protein and nucleotide sequences," FEMS Microbiology Letters, May 1, 1999, vol. 174, No. 2, pp. 247-250.
Tumban et al., "A pan-HPV vaccine based on bacteriophage PP7 VLPs displaying broadly cross-neutralizing epitopes from the HPV minor capsid protein, L2," PloS One, Aug. 17, 2011, vol. 6, No. 8, pp. 1-11.
Wang et al., "A potent anti-malarial human monoclonal antibody targets circumsporozoite protein minor repeats and neutralizes sporozoites in the liver," Immunity, Oct. 13, 2020, vol. 53, No. 4, pp. 733-744.

(A)

(B)

(C)

(A)

(B)

(C)

(D)

(D)

MALARIA IMMUNOGEN AND METHODS FOR USING SAME

CROSS-REFERENCE TO RELATED APPLICATION

This application is the § 371 U.S. National Stage of International Application No. PCT/US2020/043375, filed Jul. 24, 2020, which claims the benefit of U.S. Provisional Patent Application No. 62/878,003 filed Jul. 24, 2019, each of which is incorporated herein by reference in its entirety.

SEQUENCE LISTING

This application contains a Sequence Listing electronically submitted to the United States Patent and Trademark Office via EFS-Web as an ASCII text file entitled "310-000151WO01_ST25.txt" having a size of 4 KB and created on Jul. 23, 2020. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect, an immunogen useful for treating malaria. Generally, the immunogen includes an immunogenic carrier and an antigenic malaria circumsporozoite protein (CSP) peptide that includes NPDPNANPNVDPNAN (amino acids 5-19 of SEQ ID NO:1) linked to the immunogenic carrier.

In some embodiments, the immunogenic carrier is a Qβ bacteriophage virus-like particle (VLP).

In some embodiments, the immunogenic carrier is linked to the CSP peptide through a succinimidyl-6-[β-maleimido-propionamido]hexanoate (SMPH) cross-linker molecule.

In another aspect, this disclosure describes a composition that includes any embodiment of the immunogen summarized above.

In another aspect, this disclosure describes an immunogenic composition that includes any embodiment of the immunogen summarized above and at least one adjuvant.

In another aspect, this disclosure describes a method of treating malaria in an individual. Generally, the method includes administering to the individual a therapeutically effective amount of any embodiment of the immunogen summarized above.

In some embodiments, the immunogen is administered prophylactically.

In some embodiments, the method further includes administering to the individual at least one additional therapeutic agent for treating malaria.

In another aspect, this disclosure describes a nucleic acid encoding any embodiment of the immunogen summarized above. In some embodiments, the nucleic acid is a portion of an expression vector.

In another aspect, this disclosure describes a host cell that includes any embodiment of the nucleic acid that encodes the immunogen.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION OF ILLUSTRATIVE EMBODIMENTS

Figure 1:
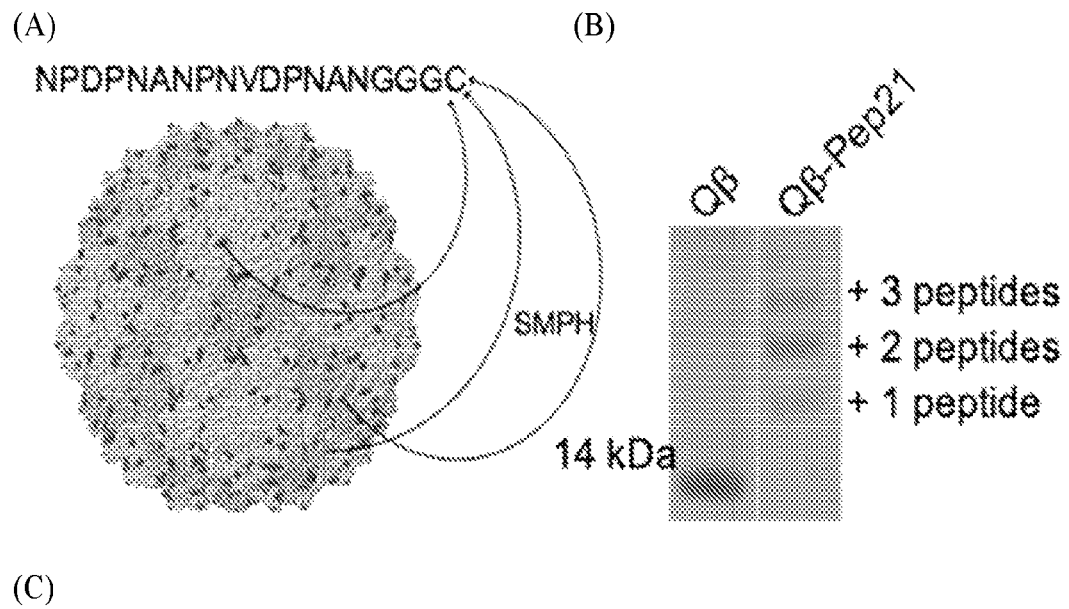
FIG. 1. Characterization of CIS43CLPs. (A) Schematic representation of CIS43 VLP conjugation. A 19-amino acid peptide (SEQ ID NO:4) including the CIS43 mAb epitope (amino acids 5-19 of SEQ ID NO:1) and a GGGC linker (SEQ ID NO:2) was conjugated to surface-exposed lysine residues (shown in red) on the coat protein of Qβ bacteriophage VLPs using the bifunctional crosslinker SMPH. (B) SDS-PAGE analysis of unconjugated (left lane) or CIS43 conjugated (right lane) Qβ VLPs. The ladder of bands in the CIS43 VLP lane reflect individual copies of coat protein modified with one, two, or more copies of the CIS43 peptide. (C) Binding of the CIS43 mAb to CIS43 VLPs (red) or wild-type (unmodified) Qβ VLPs (blue) as measured by ELISA.
Figure 1:
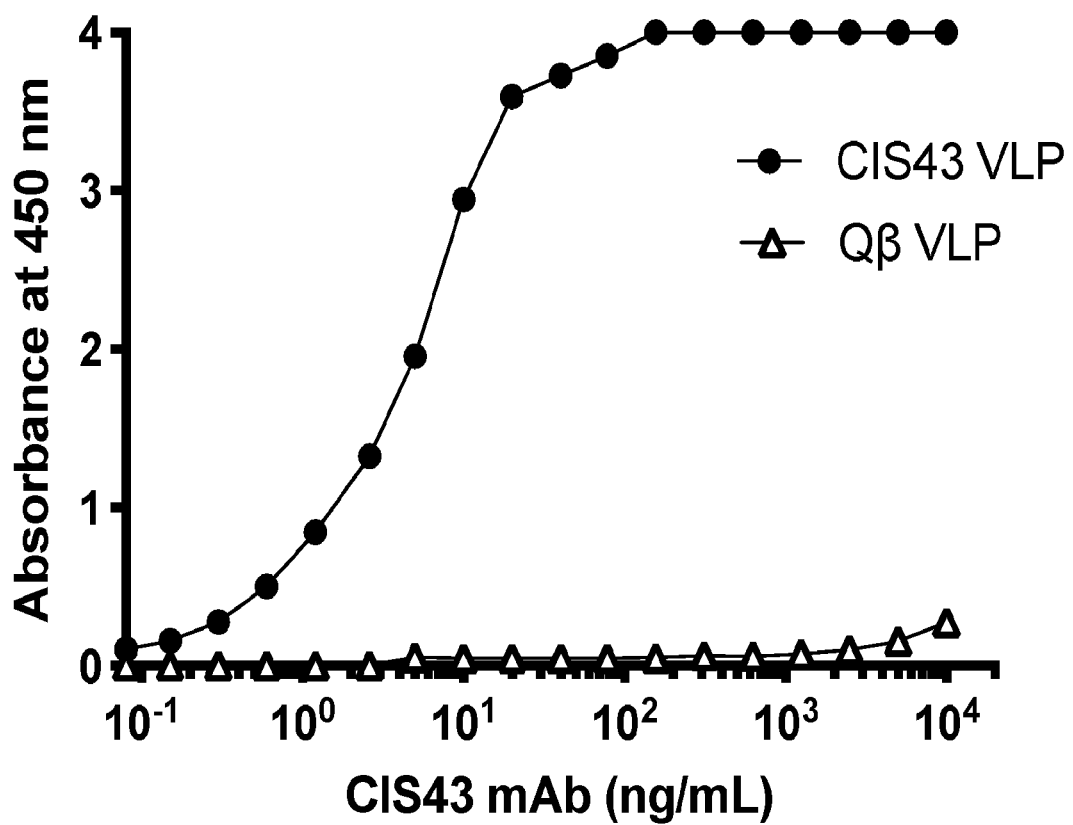

Malaria is a significant global public health concern. A disproportionate share of malarial disease and deaths occurs in Africa and is caused by infection with the *Plasmodium falciparum* parasite. *P. falciparum* (Pf) infection is initiated when the Anopheles mosquito injects sporozoites into the blood stream of a human host. Sporozoites are transported quickly to the liver where they transiently multiply within hepatocytes, producing merozoites, which then enter the blood stream where they invade red blood cells (RBCs), replicate further, and cause the symptoms and pathology of malaria.

A number of different malaria vaccine strategies have been proposed, including vaccines that target transmission, the erythrocytic stage in which symptoms occur, and the pre-erythrocytic stage. A pre-erythrocytic vaccine that effectively blocks malaria infection of hepatocytes could potentially provide sterilizing immunity against malaria. However, development of such a vaccine has been complicated by a number of factors, including (1) natural immunity to the pre-erythrocytic stage is weak and ineffective, (2) surface antigens expressed on sporozoites are antigenically variable, and (3) high titers of circulating antibody are likely required to effectively inhibit infection.

Most attempts to develop pre-erythrocytic vaccines have targeted the malaria circumsporozoite protein (CSP). CSP is the most abundant protein on the surface of the malaria sporozoite and is an attractive vaccine target because anti-CSP antibodies prevent the malaria parasite from reaching the liver and establishing infection. CSP is the target of RTS,S/AS01 (also referred to as RTS,S), the most advanced malaria vaccine. While the clinical implementation of RTS,S is a notable achievement, this vaccine confers only moderate (30-50%) protection against clinical infection, and immunity rapidly declines. Thus, there remains a need for a malaria vaccine with higher potency and provides more durable immune responses than the RTS,S vaccine.

Most previous CSP-targeted vaccines have used full-length or near full-length antigen. RTS,S, for example, contains a large domain of the CSP central-repeat region and most of its C-terminal domain. While a subset of antibodies elicited by RTS,S are protective, using large domains of an antigen can be problematic as critical epitopes may be hidden or immunologically subdominant.

This disclosure describes an alternate approach that involves an immunogen designed to target epitopes that are defined by antibodies from infected patients that inhibit subsequent infection. This disclosure assesses the immunogenicity and prophylactic efficacy of a vaccine targeting an epitope of circumsporozoite protein (CSP), the major surface antigen on *Plasmodium falciparum* sporozoites. Using a virus-like particle (VLP)-based vaccine platform technology, the junctional region between the N-terminal and central repeat domains of CSP was targeted. This region of CSP is highly conserved (present in 99.88% of Pf isolates) and is the epitope recognized by monoclonal antibodies, including mAb CIS43 (Kisalu et al., 2018, *Nat Med* 24:408-416), that have been shown to inhibit *P. falciparum* entry into hepatocytes. This epitope is not present in the RTS,S vaccine.

The monoclonal antibody CIS43 was isolated from a subject immunized with an attenuated Pf whole-sporozoite vaccine (the Sanaria PfSPZ Vaccine). Passive immunization with CIS43 inhibits infection of mice from both intravenous and mosquito challenge with a transgenic strain of *Plasmodium berghei* (Pb) in which the PbCSP has been replaced with full-length PfCSP (Pb/PfCSP). The CIS43 epitope was mapped to a 19-amino-acid region of CSP (amino acids 97-115; PADGNPDPNANPNVDPNAN; SEQ ID NO:1) that is within the junctional domain between the N-terminus and central repeat domains of CSP.

The discovery of a novel site of vulnerability within CSP has several clinical implications. First, neutralizing mAbs can be used as prophylactic treatment in humans traveling to malaria endemic areas. CIS43, for example, has entered Phase I trials for prophylactic treatment of clinical malaria in humans. Second, these data suggest that the junctional domain of CSP is a promising target for vaccine development. However, no effectively vaccines targeting this region have been reported in the literature. Mice immunized with a vaccine consisting of a 19-amino-acid peptide encompassing the MGG4 epitope conjugated to keyhole limpet hemocyanin (KLH) failed to block sporozoite invasion of hepatocytes (Tan et al., 2018. *Nat Med.* 24(4):401-407). More broadly, there are significant challenges to developing an effective liver-stage vaccine targeting malaria sporozoites. Sporozoites can reach hepatocytes in less than an hour following infection, limiting the window of time in which immune responses can act. In addition, a single infected hepatocyte can seed the blood stage of the malaria life cycle, meaning that effective immunity likely must be sterilizing. Thus, there is a high barrier for vaccine-mediated protection—an effective vaccine must elicit very high levels of circulating antibodies, and these antibodies must be long-lived.

As a potential solution, this disclosure reports the effectiveness of a virus-like particle (VLP)-based vaccine targeting the CIS43 epitope. VLPs are non-infectious, self-assembling particles that are derived from viral structural proteins that can be used as standalone vaccines, but also can be applied as platforms for vaccine development. VLP-based vaccine design exploits the intrinsic ability of viral structural proteins to self-assemble into highly immunogenic, multivalent particles. These multivalent structures are highly effective at stimulating strong antibody responses by promoting B cell receptor crosslinking, leading to robust and long-lasting antibody responses against diverse target antigens.

This disclosure therefore describes the development and characterization of a bacteriophage VLP-based vaccine targeting the CIS43 epitope. CIS43 VLPs elicit strong and long-lasting antibody responses against CSP in both mice and macaques. The elicited antibodies inhibit malaria infection via intravenous challenge using Pb/PfCSP parasites. This vaccine combines amino acids sequence from SEQ ID NO:1, VLP display technology, and, optionally, an adjuvant.

VLP Display

Many viral structural proteins have an intrinsic ability to self-assemble into virus-like particles (VLPs), which structurally resemble the virus from which they were derived but, because they lack viral genomes, are absolutely noninfectious. VLPs not only can serve as stand-alone vaccines, but because their particulate nature and multivalent structure provoke strong immune responses, they can be used as platforms to enhance the immunogenicity of heterologous antigenic targets. For example, when short peptide epitopes are displayed in a highly repetitive, multivalent fashion on VLPs, peptide-specific B cells are strongly activated, leading to high-titer, long-lasting antibody responses. VLPs derived from diverse virus types can serve as effective platforms for antigen display. The immunogens described herein are based on VLPs derived from a family of related single-stranded RNA bacteriophages, including MS2, PP7, AP205, and Qβ. These VLPs can be produced by expressing a single viral structural protein, called coat, from a plasmid in a bacterium. In some embodiments, a peptide may be displayed on a VLP by conjugating the peptide to the VLP through a succinimidyl-6-[β-maleimidopropionamido] hexanoate (SMPH) cross-linker molecule. This technique results in VLPs that display target peptides at high valency, usually 180-360 peptides per VLP, and confers strong immunogenicity to displayed epitopes.

ADVAX Adjuvant Platform

While alum remains the dominant adjuvant used in human vaccines worldwide, it has shown poor utility in malaria vaccines, with oil emulsions and more complex adjuvant combinations such as AS01 delivering more favorable results in human studies. However, oil emulsion adjuvants are associated with high reactogenicity and RTS,S/AS01 vaccine protection attenuates rapidly. A major malaria vaccine challenge is to find a suitable adjuvant platform that overcomes these obstacles. This adjuvant platform needs to be able to drive strong and long-lasting humoral and cellular immune responses while being non-reactogenic and safe for use in young children. ADVAX (Vaxine Pty, Ltd., Adelaide, Australia) was developed as a polysaccharide particle adjuvant platform based on the plant sugar, delta inulin (Petrovsky et al., 2015, *Vaccine* 33:5920-5926) to further enhance its adjuvant potency, ADVAX can be co-formulated with low amounts of toll-like receptor (TLR) agonists such as CpG oligonucleotides that activate TLR9 and/or imidazoquinoline amines that activate TLR7 and/or TLR8. This results in highly effective vaccine formulations that can induce immunity after just one immunization sufficient to inhibit infection, generate longer lasting and more broadly cross-neutralizing antibodies, and production of durable memory CD4 and CD8 T cell responses (Petrovsky et al., 2015, *Vaccine* 33:5920-5926). These adjuvant formulations can be designed to shape the immune response in any desired direction, e.g. Th1, Th2, or Th17, that correlates best with immunity.

Construction and Antigenicity of CIS43 VLPs

To assess whether VLP display could be used to induce potent, long lasting anti-CSP responses, a vaccine was engineered in which a 15-amino-acid peptide representing CSP amino acids 101-115 (amino acids 5-19 of SEQ ID NO:1) was displayed multivalently on the surface of Qβ bacteriophage VLPs, to produce CIS43-VLPs. The CSP peptide was conjugated to surface lysine residues on Qβ bacteriophage VLPs using a bifunctional crosslinker succinimidyl-6-[β-maleimidopropionamido]hexanoate (SMPH) (FIG. 1A). Conjugation efficiency was measured by SDS-PAGE analysis. Successful peptide conjugation is indicated by an increase in the molecular weight of Qβ coat protein subunits, reflecting conjugation of one or more peptides to Qβ coat protein (FIG. 1B, right lane). More than half of all coat protein bound two or more copies of peptide, suggesting that the particles are decorated with the peptide in a dense and multivalent fashion. On average, approximately 360 copies of peptide were conjugated to each Qβ VLP.

To assess the antigenicity of the vaccine, called CIS43-VLP, the ability of mAb CIS43 to bind to CIS43-VLPs was measured by ELISA. FIG. 1C shows that CIS43 reacts strongly with the VLPs. This suggests that the CIS43 epitope peptide is displayed on the Qβ particles in a manner that emulates its antigenic conformation on CSP.

CIS43 VLPs Induce High Titer Antibody Responses Against CSP

Figure 2:
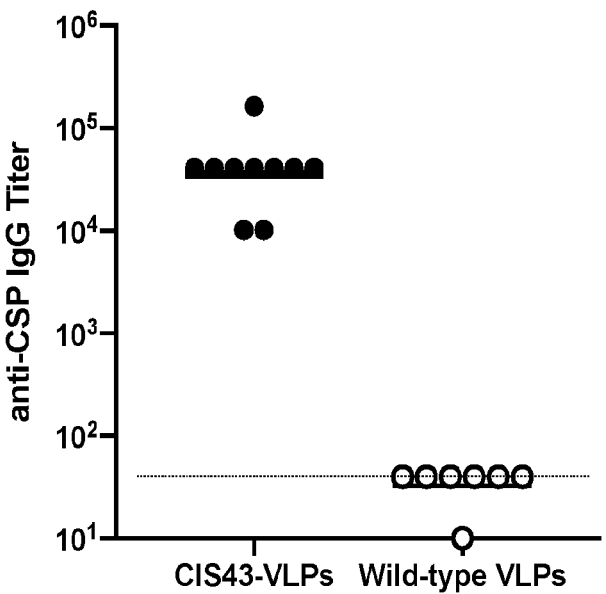
FIG. 2. End-point dilution IgG titers against PfCSP in sera from mice given two doses, at a three-week interval, of 5 µg CIS43-VLPs (or control wild-type VLPs) without adjuvant.
Figure 3:
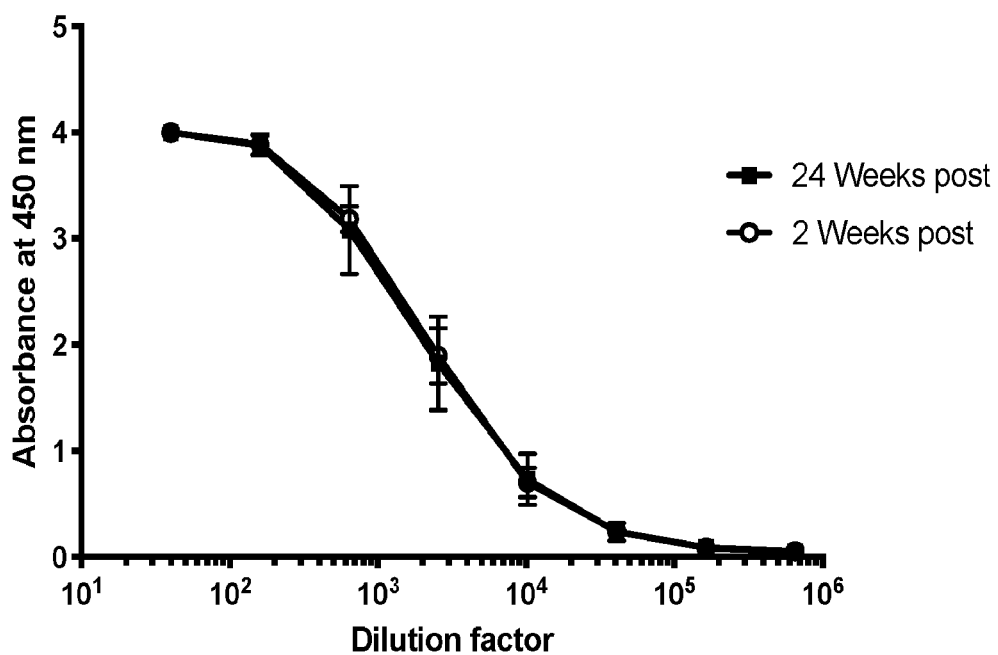
FIG. 3. Anti-CSP antibody levels in mice immunized twice with CIS43-VLPs. Sera was taken two and 24 weeks after the second immunization.

To test the immunogenicity of the VLPs, mice were immunized with two doses of 5 μg of CIS43-VLPs (at a 3-week interval, without any exogenous adjuvant), sera were taken, and then antibody responses against full-length recombinant *P. falciparum* CSP were measured by end-point dilution ELISA. FIG. 2 shows that CIS43-VLP-immunized mice had strong antibody responses against CSP. Anti-CSP antibody levels did not measurably decline 24 weeks months post-immunization (FIG. 3).

Figure 6:
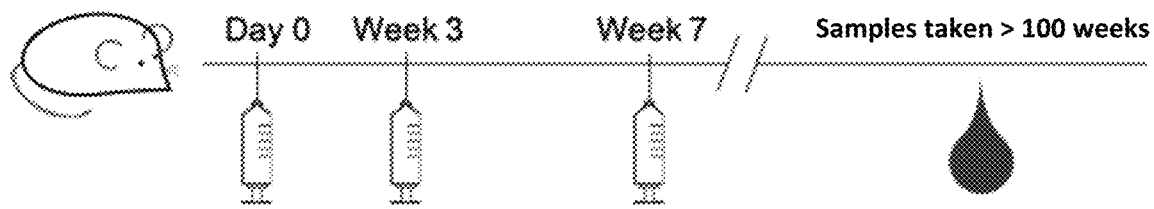
FIG. 6. CIS43 VLPs elicit high titer and long-lasting antibody responses against PfCSP. (A) CIS43 VLP immunization scheme. (B) IgG titers against CIS43 peptide or CSP were 5determined using sera collected six weeks after the initial vaccination. Balb/c mice were immunized with 5 µg of CIS43 VLPs (n=5; red symbols) or 5 µg of WT Qβ VLPs (n=3; blue symbols). Each data point represents an individual mouse and lines represent the geometric mean titers of each group. Statistical significance between groups was determined by t-test (****; $p<0.0001$) (C) Geometric mean IgG titers were determined longitudinally for over 100 weeks after the initial vaccination. Note that three of the mice in the CIS43 VLP vaccinated group died of old age (at weeks 56, 60, & 60) prior to the completion of the study. (D) Sera from CIS43-VLP-immunized mice bind to CSP peptides. CIS43: NPDPNANPNVDPNAN (amino acids 5-19 of SEQ ID NO:1); MGG4-15mer: KQPADGNPDPNANPN (SEQ ID NO:5); MGG4-19mer: KQPADGNPDPNANPNVDPN (SEQ ID NO:6); CSP 5D5: EDNEKLRKPKHKKLK (SEQ ID NO:7); CSP central repeat peptide: NANPNANPNANPNANPNA (SEQ ID NO:8); Mal: NANPNVDPNANPNANPNANP (SEQ ID NO:9).
Figure 6:
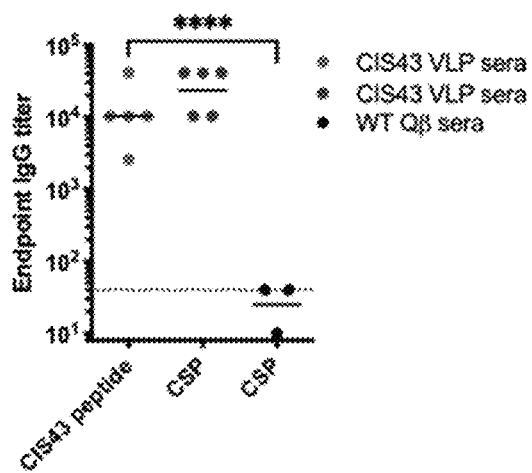
Figure 6:
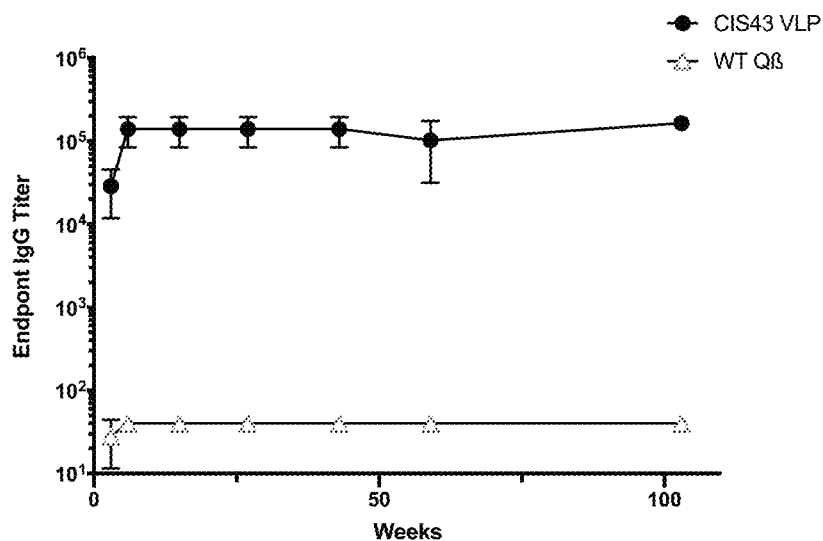
Figure 6:
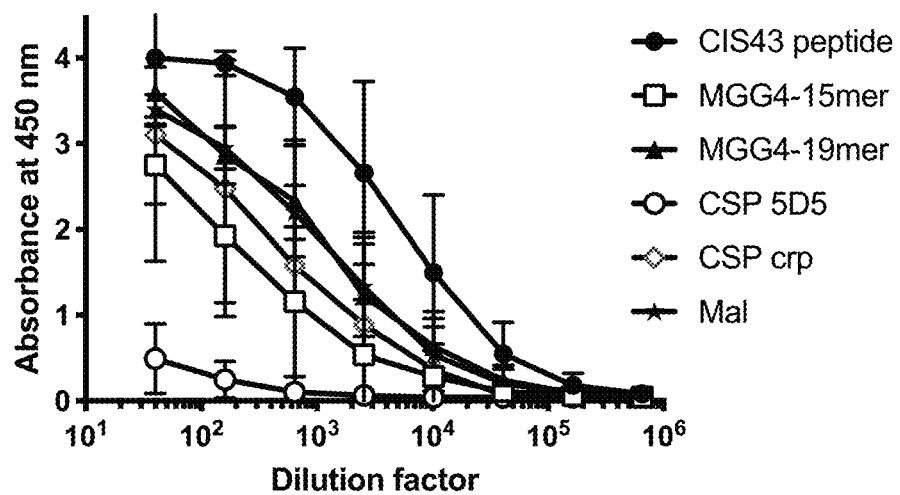

Subsequently, Balb/c mice were intramuscularly immunized with 5 µg of CIS43 VLPs or 5 µg WT Qβ VLPs as a negative control, and boosted with the same dose at three weeks and seven weeks (FIG. 6A). Three weeks following the final boost, antibody responses against the CIS43 peptide and full-length recombinant P. falciparum CSP (rPfCSP) were measured by end-point dilution ELISA. Whereas negative control sera collected from WT-Qβ-VLP-immunized mice did not show reactivity to the CIS43 peptide or rPfCSP, CIS43 VLPs elicited strong anti-peptide and anti-rPfCSP antibody responses (FIG. 6B). The antibody titer to rPfCSP was slightly higher than the anti-CIS43 peptide titer. Similar antibody titers were observed in vaccinated C57BL/6 mice (data not shown). To interrogate the binding promiscuity of elicited anti-CSP antibodies from immunized Balb/c mice, sera were tested against several CSP peptides by peptide ELISA. While anti-sera bound most strongly to the peptide corresponding to the CIS43 epitope, the sera cross-reacted with several other CSP-derived peptides, particularly those peptides which contained one or more of the NANP motifs found in the CSP central repeat domain (FIG. 6D).

Next, serum was collected regularly for nearly two years after the third immunization and anti-rPfCSP IgG titers were determined by ELISA. Anti-rPfCSP IgG titers were stable over this period, nearly spanning the lifetime of the mice (FIG. 6C). Together, these experiments illustrate that CIS43 VLPs elicit robust and long-lived antibody responses.

Immunization With CIS43 VLPs Inhibits Infection From Intravenous Challenge With Plasmodium To determine whether immunization with VLP-CIS43 could inhibit malaria infection in vivo, a well-characterized mouse infection model for testing CSP-targeted vaccines was used. In this model mice are challenged with transgenic P. berghei (Pb) that have been engineered to express full-length PfCSP (in place of PbCSP) and a luciferase reporter (Pb-Pf-Luc) (Flores-Garcia et al., 2019. Malar J. 18(1):1-9). 42 hours after infection, liver-stage parasite burden can be quantitated by luciferase levels.

Figure 4:
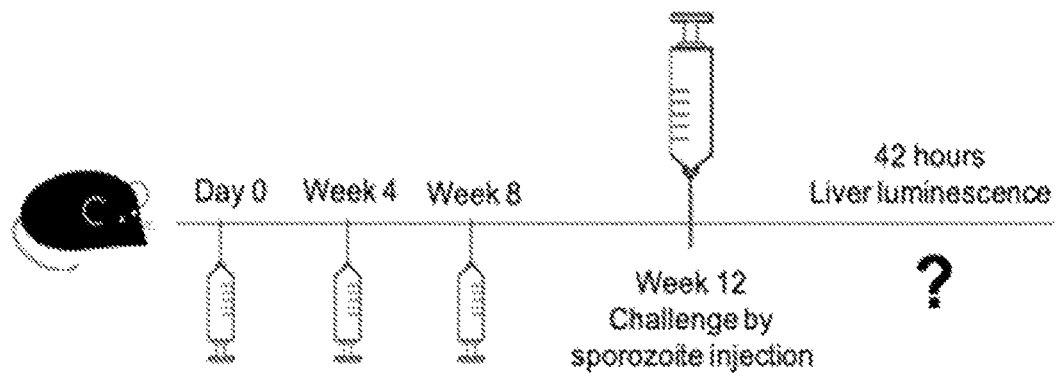
FIG. 4. Immunization with CIS43 VLPs without exogenous adjuvant confers partial immunity from *Plasmodium* infection. (A) Immunization and challenge scheme. (B) Parasite liver load (as measured by luminescence) in vaccinated or naive mice following challenge by sporozoite injection. Statistical comparison, as measured by one-way ANOVA followed by Dunnett's multiple comparison test, shows a statistically significant reduction in liver parasite burden in mice immunized with CIS43 VLPs compared to unimmunized mice. ns; not significant, ***; $p<0.001$. (C) Percent inhibition of liver infection, as calculated from luminescence data. Inhibition of infection is calculated relative to the geometric mean signal in the naïve, challenged group of mice.
Figure 4:
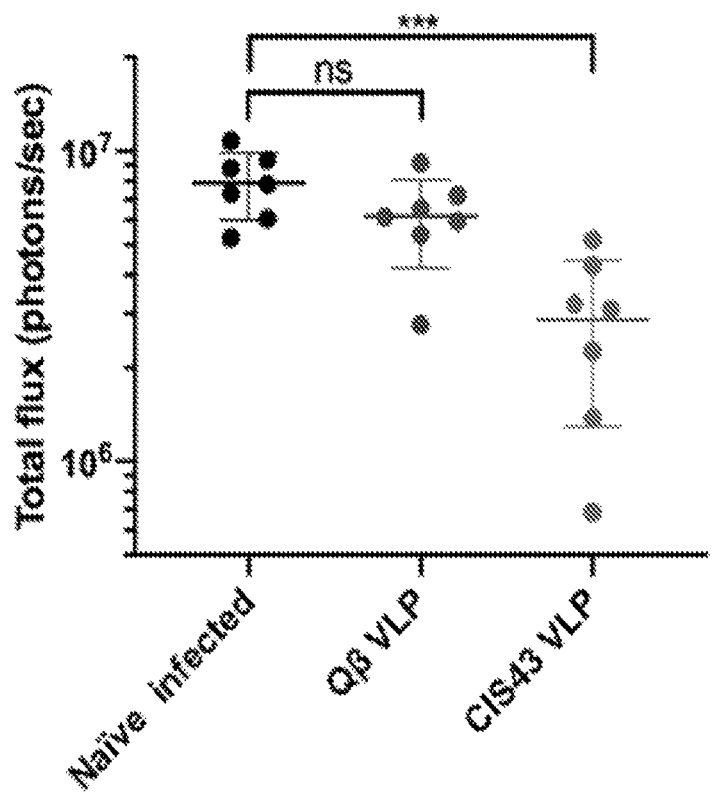
Figure 4:
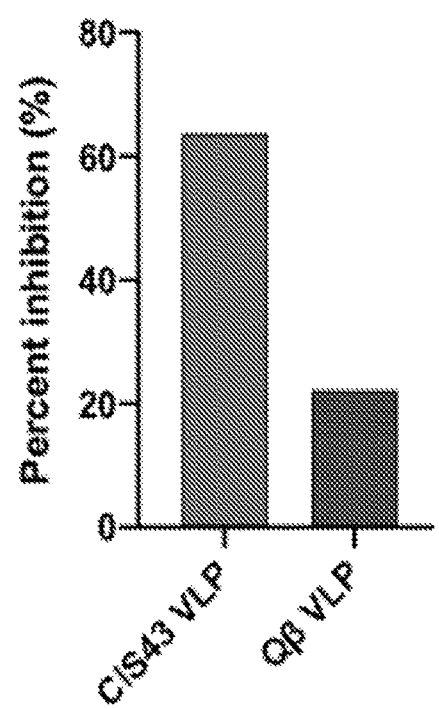

Mice were immunized three times with CIS43 VLPs or, as a negative control, wild-type (WT) Qβ VLPs, and then were challenged by intravenous injection of 1000 Pb-Pf-Luc sporozoites four weeks following the final vaccine boost (FIG. 4A). Liver luciferase levels were compared to unimmunized (naïve) mice. Mice immunized with CIS43 VLPs had a significantly reduced liver-stage parasite burden compared to naive mice or controls vaccinated with WT VLPs (FIGS. 4B and 4C). No statistical difference was observed between naïve infected mice and mice immunized with WT Qβ VLPs. These data suggest that immunization with unadjuvanted CIS43 VLPs provides partial (~60%) inhibition of parasite liver invasion and protection from malaria infection in a rigorous challenge mouse model.

ADVAX Adjuvants Increase the Immunogenicity of CIS43 VLPs

Figure 5:
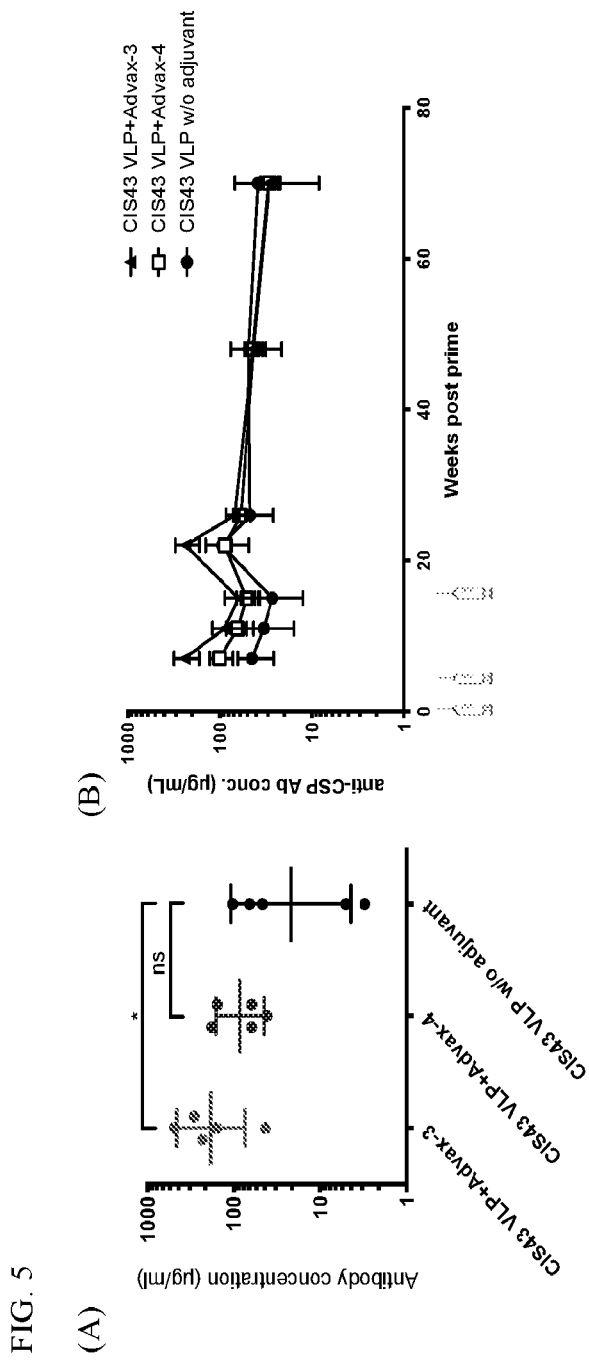
FIG. 5. ADVAX adjuvants (Vaxine Pty, Ltd., Adelaide, Australia) enhance CIS43 VLP immunogenicity. (A) Anti-CSP antibody concentrations in Balb/c mice immunized two times with CIS43 VLPs with or without ADVAX-3 or ADVAX-4 (n=5/group). ns; not significant, *; $p<0.05$. (B) Kinetics of anti-CSP antibody concentrations in Balb/c mice immunized three times with CIS43 VLPs with or without adjuvant. Mice were immunized three times: at week 0, week 4, and week 18, and anti-CSP antibody concentrations were measured at various timepoints following immunization.
Figure 9:
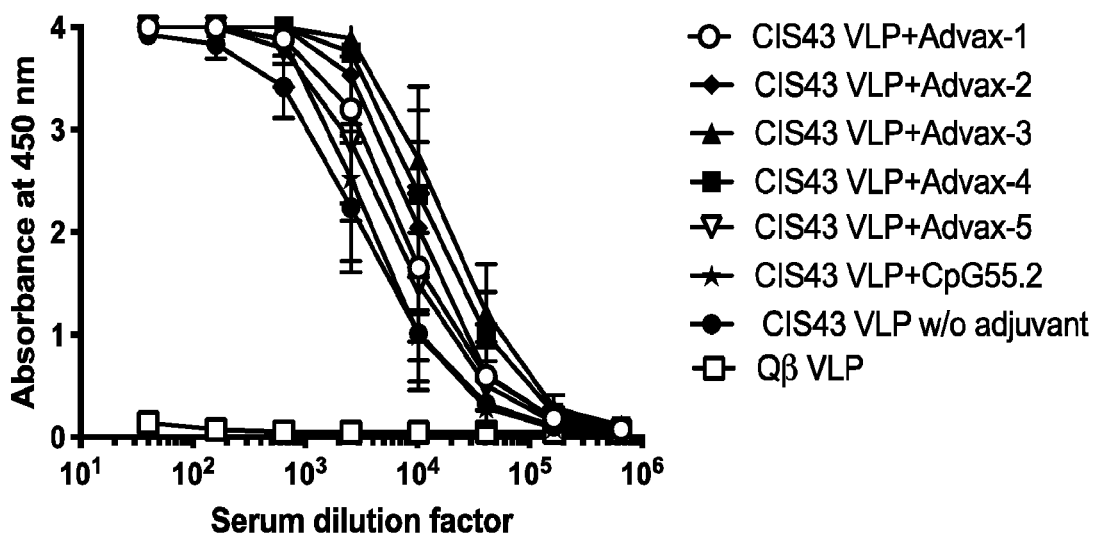
FIG. 9. ADVAX adjuvants enhance anti-CSP IgG response to CIS43 VLP immunization Groups of Balb/c mice (n=5) were immunized with CIS43 VLPs adjuvated with different ADVAX adjuvant formulations or CpG oligonucleotides. Unadjuvanted CIS43 VLPs and WT Qβ VLPs were used as controls.

As a strategy to increase antibody titers elicited by CIS43 VLPs, the compatibility of CIS43 VLPs with ADVAX adjuvants was tested. ADVAX adjuvants contain delta inulin polysaccharides that can enhance cellular and/or humoral immune responses to a variety of antigens. Mice were immunized three times with CIS43 VLPs in combination with five different ADVAX formulations (ADVAX-1-5), CpG oligonucleotides, or without exogenous adjuvant and then antibody titers were determined by ELISA. ADVAX adjuvants, but not CpGs, increased anti-CSP antibody titers relative to unadjuvanted CIS43 VLPs (FIG. 9). Amongst the adjuvants that were tested, ADVAX-3 and ADVAX-4 had the greatest boosting effect on anti-CSP titers. To more carefully measure the impact of adjuvants, anti-CSP antibody concentrations were quantified in vaccinated mice by linear regression analysis using a standard curve generated with the mouse anti-CSP mAb 2A10 (Anker et al., 1990. Eur J Immunol. 20(12):2757-2761). After two immunizations, mice immunized with unadjuvanted CIS43 VLPs generated a mean anti-CSP IgG level of 44 µg/mL. Formulation of CIS43 VLPs with ADVAX-3 or ADVAX-4 significantly boosted anti-CSP IgG concentrations by 5.5-fold and 2.3-fold, respectively (FIG. 5A).

To evaluate the longevity of the response, anti-CSP IgG responses were followed over time. FIG. 5B shows that antibody responses induced by unadjuvanted CIS43 VLPs were stable over time. ADVAX adjuvants, particularly ADVAX-3, provided a boost in antibody responses that declined fairly rapidly following the second immunization, suggesting that some of the antibody responses were derived from short-lived plasma cells. Antibody titers rebounded to peak concentrations after a second boost 18 weeks after the primary immunization. The anti-CSP IgG concentrations remained stable following the initial decline after the second boost (FIG. 5B).

Figure 7:
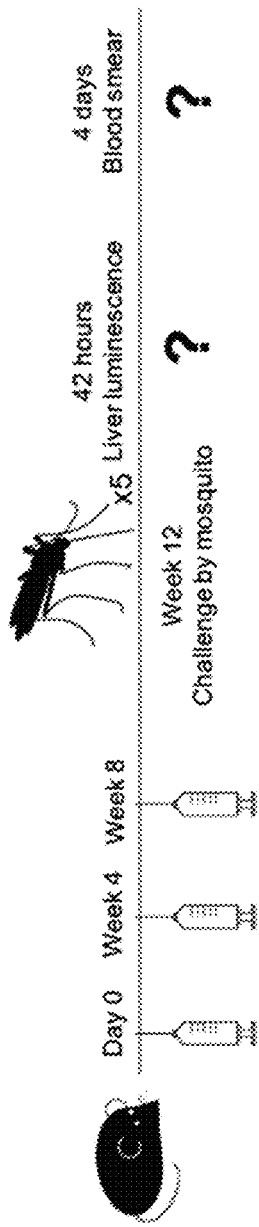
FIG. 7. Vaccination with CIS43 VLPs in combination with ADVAX adjuvants inhibits malaria infection. (A) Immunization and challenge scheme. Groups of mice (n=6 or 7/group) were immunized three times and then challenged with five Pb-Pf-Luc infected mosquitos. Liver luminescence was evaluated 42 hours following mosquito challenge. (B) Parasite liver load (as measured by luminescence) in CIS43 VLP vaccinated or control mice following mosquito challenge. Mann-Whitney test was used to statistically compare each group to the unimmunized (naïve) group. *; p<0.05, **; p<0.01. (C) Percent inhibition of liver infection, as calculated from luminescence data. Inhibition of infection is calculated relative to the geometric mean signal in the negative control groups of mice. (D) Avidity of anti-CSP antibodies elicited following immunization with CIS43 VLPs with or without adjuvant.
Figure 7:
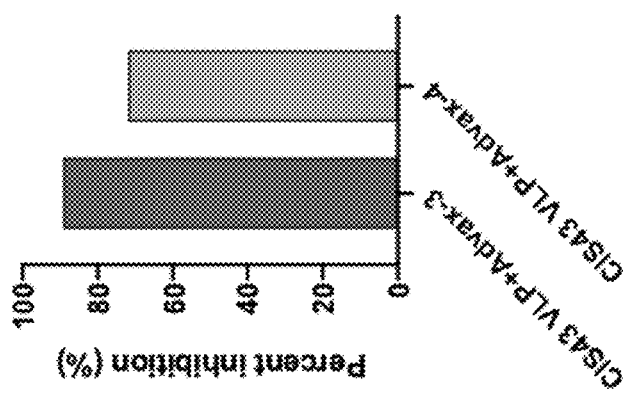
Figure 7:
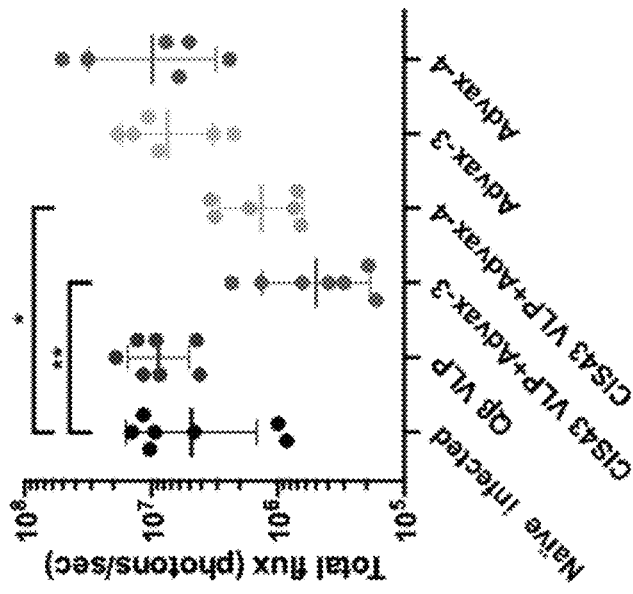
Figure 7:
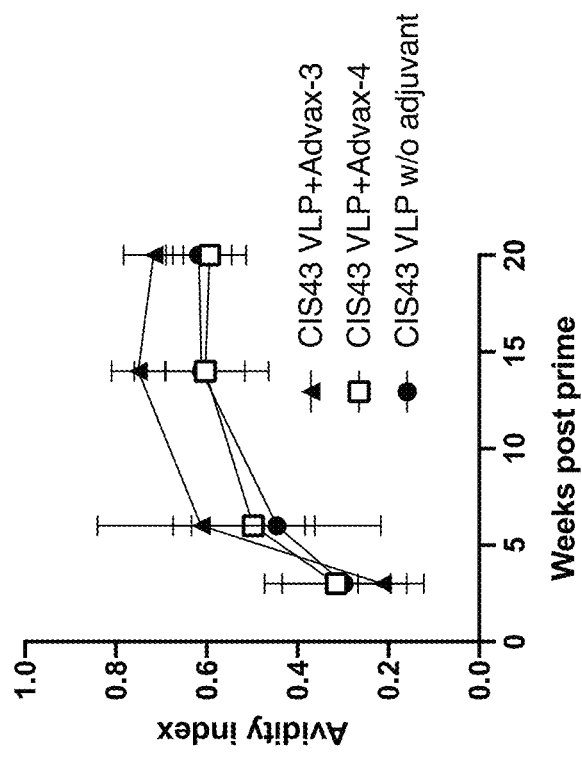

Vaccination With CIS43 VLPs Combined With ADVAX-3 or ADVAX-4 More Strongly Inhibits Plasmodium Infection To evaluate the protection elicited by CIS43 VLPs adjuvanted with ADVAX-3 or ADVAX-4, C57BL/6 mice (n=7/group) were vaccinated with CIS43 VLPs with adjuvant, or with adjuvant alone, and then were challenged with Pb-Pf-Luc sporozoites. In this experiment, mice were challenged with live parasite-carrying mosquitoes in order to more closely recapitulate the conditions of natural infection (FIG. 7A). Mice immunized with CIS43 VLPs adjuvanted with ADVAX-3 or ADVAX-4 showed significantly lower parasite liver loads compared to the naïve group, mice immunized with either adjuvant alone, or wild-type Qβ VLPs (FIG. 7B). Animals immunized with CIS43 VLPs adjuvanted with ADVAX-3 or ADVAX-4 showed a 90% and a 72% reduction in liver parasite loads compared to naïve mice, respectively. When liver loads were compared in these two groups with an aggregate of all of the negative control groups, CIS43 VLPs with ADVAX-3 reduced liver load by 93%, while CIS43 VLPs with ADVAX-4 reduced liver load by 82% (FIG. 7E). Despite these reductions in liver load, all of the mice in this study developed parasitemia by day 5 post-infection, as evaluated by blood smears. These results demonstrate that a single epitope-targeting CIS43 VLPs vaccine is capable of stimulating high antibody responses that confers a robust, although not sterilizing, level of protection from liver infection in a mouse model.

In clinical trials of RTS,S/AS01, increased antibody avidity, along with antibody concentration, correlated with increased protection from clinical malaria. To understand how avidity of CIS43 VLP-elicited antibody changes over time and in response to added adjuvant, the avidity index (AI) of antibodies against CSP was evaluated using a chaotrope-based avidity assay. The mean AI of each group increased after each immunization, culminating in a high mean AI value (>0.5) in all of the groups following the third immunization (FIG. 7D). Among the three vaccine groups tested, ADVAX-3 adjuvanted CIS43 VLPs elicited anti-CSP antibodies with the highest avidity (FIG. 7D).

CIS43 VLPs Elicit Anti-CSP Antibody Responses in Non-Human Primates

Figure 8:
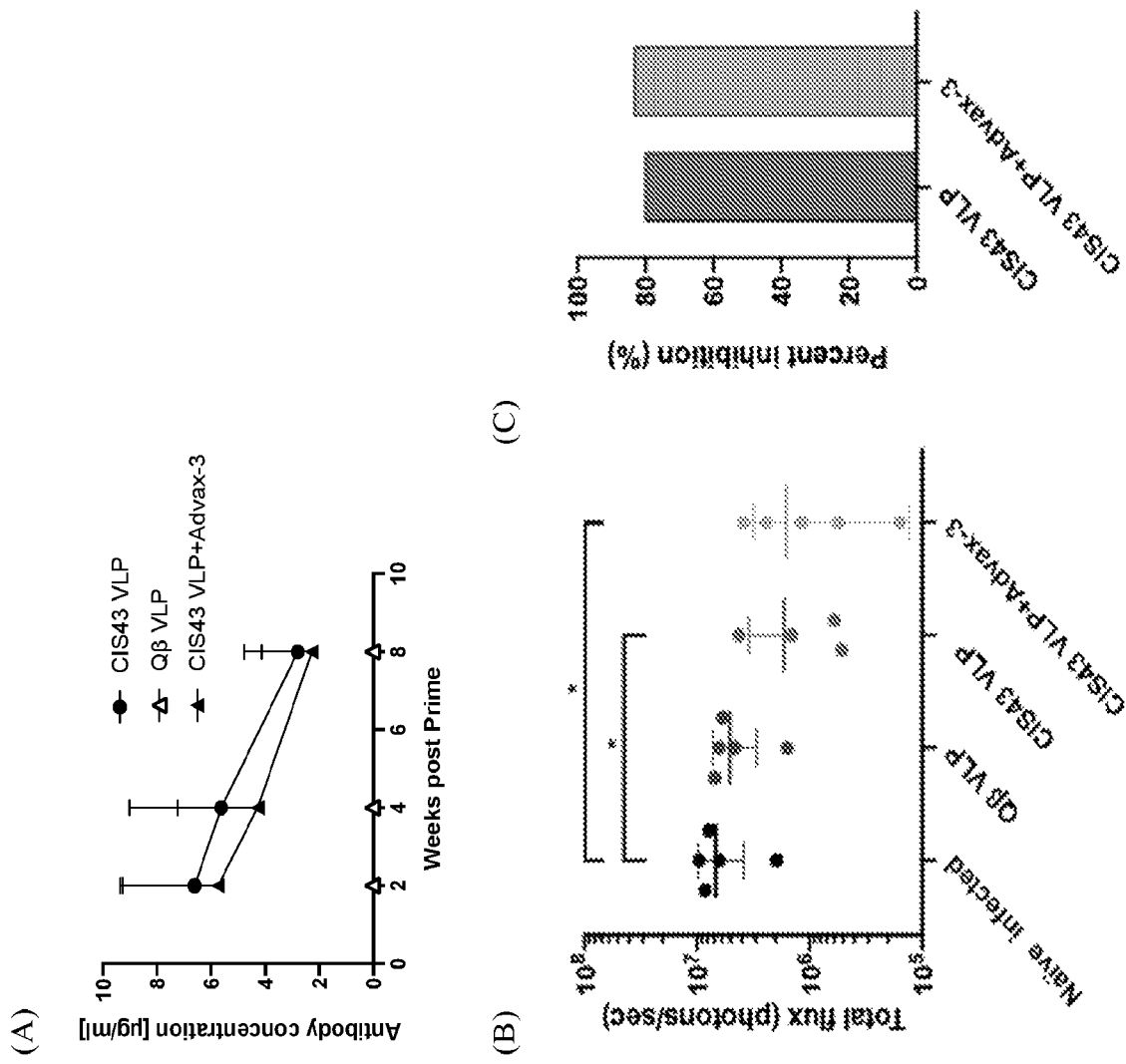
FIG. 8. Immunization of cynomolgus monkeys with CIS43 VLPs elicits antibodies that can inhibit malaria infection. (A) IgG concentrations in cynomolgus monkeys immunized at week 0 and week 4 with CIS43 VLPs with or without ADVAX-3 adjuvant (n=3/group). WT Qβ VLPs were used as a negative control. (B) Parasite liver load (as measured by luminescence) in mice (n=4-5/group) that received an intravenous injection of 500 µl of sera from immunized cynomolgus monkeys. Two hours following serum transfer, mice were challenged with five Pb-Pf-Luc infected mosquitoes. Mann-Whitney test was used to statistically compare each group to the group that received an intravenous injection with PBS. (C) Percent inhibition of liver infection, as calculated from luminescence data. Inhibition of infection is calculated relative to the geometric mean signal in the groups of mice treated with PBS.

CIS43 VLP immunogenicity in non-human primates was evaluated by immunizing groups (n=3) of cynomolgus monkeys with unadjuvanted CIS43 VLPs or CIS43 VLPs adjuvanted with ADVAX-3. All of the macaques developed anti-CSP antibodies (FIG. 8A), but there was heterogeneity in the responses, possibly due to the diverse ages and sizes of the animals in the study. To investigate whether serum from CIS43 VLP-immunized cynomolgus monkeys can inhibit infection, monkey sera were passively transferred into naïve C57BL/6 mice, then the mice were challenged mice with Pb-Pf-Luc by mosquito infection. Macaque sera was obtained two weeks after the second immunization, pooled by immunization group, then and used to intravenously immunize mice. The mice were rested for two hours after immunization before being subjected to mosquito challenge. As before, parasite liver load was evaluated by liver luminescence.

A statistically significant decrease in luminescence was observed in mice passively immunized with pooled sera from macaques immunized with unadjuvanted CIS43 VLP group and ADVAX 3-adjuvanted CIS43 VLPs, but not using sera from macaques immunized with control VLPs. Sera from monkeys immunized with unadjuvanted CIS43 VLPs reduced liver parasitemia by 80.5%, and sera from ADVAX 3-adjuvanted CIS43 VLPs reduced liver parasitemia by 83.4%. Thus, these data show that non-human primates immunized with CIS43 VLPs elicit antibody responses that are capable of inhibiting hepatocyte invasion.

Thus, this disclosure describes a VLP-based immunogen that specifically targets CSP. These particles are highly immunogenic in both mouse and macaque models and elicit a long-lived antibody response. To increase the immunogenicity of CIS43 VLPs, the CIS43 VLPs can be combined with an adjuvant. Suitable adjuvants include, but are not limited to, delta inulin polysaccharide-based ADVAX adjuvants. In particular, combining CIS43 VLPs with ADVAX-3 or ADVAX-4 yields higher anti-CSP antibody titers than unadjuvanted CIS43 VLPs. In a rigorous challenge model, the CIS43 VLP vaccine inhibits sporozoite entry into the liver in mice. These results were recapitulated with passive transfer of sera from CIS43 VLP-immunized macaques into mice.

The immunogen includes an antigenic CSP peptide (also referred to herein as a "a CSP-targeting peptide") such as, for example, amino acids 5-19 the amino acid sequence of SEQ ID NO:1, the amino acid sequence of SEQ ID NO:5, the amino acid sequence of SEQ ID NO:6, the amino acid sequence of SEQ ID NO:7, the amino acid sequence of SEQ ID NO:8, the amino acid sequence of SEQ ID NO:9, a structurally similar peptide, or a combination of two or more of the foregoing. For example, the immunogen can include a VLP that displays more than one population of antigenic CSP peptides—e.g., a first population of antigenic CSP peptides that includes amino acids 5-19 the amino acid sequence of SEQ ID NO:1 and a second population of antigenic CSP peptides that includes the amino acid sequence of SEQ ID NO:5 (and/or the amino acid sequence of SEQ ID NO:6, and/or the amino acid sequence of SEQ ID NO:7, and/or the amino acid sequence of SEQ ID NO:8, and/or the amino acid sequence of SEQ ID NO:9, and/or a structurally similar peptide. Thus, the immunogen can be designed to display one, two, three, four, five, six, or more antigenic CSP peptides.

As used herein, a peptide is "structurally similar" to a reference polypeptide if the amino acid sequence of the peptide possesses a specified amount of identity compared to the reference peptide. Structural similarity of two peptides can be determined by aligning the residues of the two peptides (for example, a candidate polypeptide and amino acids 5-19 of SEQ ID NO:1) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate peptide is the peptide being compared to the reference peptide (e.g., amino acids 5-19 of SEQ ID NO:1). A candidate peptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison WI). Alternatively, peptides may be compared using the Blastp program of the BLAST 2 search algorithm, as described by Tatiana et al., (*FEMS Microbiol Lett*, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

An antigenic CSP peptide can include amino acids in addition to amino acid residues 5-19 of SEQ ID NO:1, so long as the additional amino acids do not eliminate immunogenicity toward CSP.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also includes the presence of conservative substitutions. A conservative substitution for an amino acid in an immunogenic peptide as described herein may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —$NH_2$. Likewise, biologically active analogs of a polypeptide containing deletions or additions of one or more contiguous or noncontiguous amino acids that do not eliminate a functional activity of the peptide are also contemplated.

In some embodiments, a CSP-targeting peptide as described herein can include a peptide with at least 60%, at least 66%, at least 73%, at least 80%, at least 86%, or at least 93% sequence similarity to amino acids 5-19 of SEQ ID NO:1. That is, a CSP-targeting polypeptide can include a total of no more than six, no more than five, no more than four, no more than three, no more than two, or no more than one amino acid deletions and non-conservative amino acid substitutions compared to amino acids 5-19 of SEQ ID NO:1.

In some embodiments, a CSP-targeting peptide as described herein can include a peptide with no more than six, no more than five, no more than four, no more than three, no more than two, or no more than one amino acid deletions and amino acid substitutions compared to amino acids 5-19 of SEQ ID NO:1, the amino acid sequence of SEQ ID NO:5, the amino acid sequence of SEQ ID NO:6, the amino acid sequence of SEQ ID NO:7, the amino acid sequence of SEQ ID NO:8, the amino acid sequence of SEQ ID NO:9. That is, a CSP-targeting peptide can have at least 60%, at least 66%, at least 73%, at least 80%, at least 86%, or at least 93% sequence identity to amino acids 5-19 of SEQ ID NO:1, the amino acid sequence of SEQ ID NO:5, or the amino acid sequence of SEQ ID NO:7; at least 68%, at least 73%, at least 78%, at least 84%, at least 89%, or at least 94% sequence identity to the amino acids of SEQ ID NO:6; at least 66%, at least 72%, at least 77%, at least 83%, at least 88%, or at least 94% sequence identity to the amino acids of SEQ ID NO:8; or at least 70%, at least 75%, at least 80%, at least 85%, at least 90%, or at least 95% sequence identity to the amino acid sequence of SEQ ID NO:20.

In some embodiments, a CSP-targeting peptide as described herein can be designed to provide additional sequences, such as, for example, the addition of added C-terminal or N-terminal amino acids that can, for example, facilitate purification by trapping on columns or use of antibodies. Such tags include, for example, histidine-rich tags that allow purification of polypeptides on nickel columns or linker peptide such as SEQ ID NO:2 and SEQ ID NO:3. Such gene modification techniques and suitable additional sequences are well known in the molecular biology arts.

The virus-like particle (VLP) can include any particle that includes viral protein assembled to structurally resemble the virus from which they are derived, but lack enough of the viral genome so that they are non-replicative and, therefore, noninfectious. A VLP may, therefore, include at least some of the viral genome, but the viral genome is genetically modified so that the viral genes responsible for infectivity and replication are inactivated. Exemplary VLPs include, but are not limited to, VLPs of Qβ, MS2, PP7, AP205, and other bacteriophage coat proteins, the capsid and core proteins of Hepatitis B virus, measles virus, Sindbis virus, rotavirus, foot-and-mouth-disease virus, Norwalk virus, the retroviral GAG protein, the retrotransposon Ty protein p1, the surface protein of Hepatitis B virus, human papilloma virus, human polyoma virus, RNA phages, Ty, frphage, GA-phage, AP 205-phage and, in particular, Qβ-phage, Cowpea chlorotic mottle virus, cowpea mosaic virus, human papilloma viruses (HPV), bovine papilloma viruses, porcine parvovirus, parvoviruses such as B19, porcine (PPV) and canine (CPV) parvovirues, caliciviruses (e.g. Norwalk virus, rabbit hemorrhagic disease virus [RHDV]), animal hepadnavirus core Antigen VLPs, filamentous/rod-shaped plant viruses, including but not limited to Tobacco Mosaic Virus (TMV), Potato Virus X (PVX), Papaya Mosaic Virus (PapMV), Alfalfa Mosaic Virus (AIMV), and Johnson Grass Mosaic Virus (JGMV), insect viruses such as flock house virus (FHV) and tetraviruses, polyomaviruses such as Murine Polyomavirus (MPyV), Murine Pneumotropic Virus (MPtV), BK virus (BKV), and JC virus (JCV).

The antigenic CSP peptides may be coupled to immunogenic carriers via chemical conjugation or by expression of a genetically engineered fusion partner. The coupling does not necessarily need to be direct, but can occur through linker sequences. More generally, when antigenic peptides are fused, conjugated, or otherwise attached to an immunogenic carrier, a spacer or linker sequence is typically added at one or both ends of the antigenic peptide. Such linker sequences generally include amino acid sequences recognized by the proteasome, proteases of the endosomes or other vesicular compartment of the cell.

In one embodiment, the antigenic CSP peptide may be displayed as fusion protein with a subunit of the immunogenic carrier. Fusion of the peptide can be effected by inserting the CSP antigenic peptide amino acid sequence into the immunogenic carrier primary sequence, or by fusion to either the N-terminus or C-terminus of the immunogenic carrier.

When the immunogenic carrier is a VLP, the chimeric antigenic peptide-VLP subunit can be capable of self-assembly into a VLP. VLP displaying epitopes fused to their subunits are also herein referred to as chimeric VLPs. For example, EP 0 421 635 B describes the use of chimeric hepadnavirus core antigen particles to present foreign peptide sequences in a virus-like particle.

Flanking amino acid residues may be added to either end of the sequence of the antigenic peptide to be fused to either end of the sequence of the subunit of a VLP, or for internal insertion of such peptide sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In another specific embodiment of the invention, the immunogenic carrier is a VLP of a RNA phage, preferably Qβ. The major coat proteins of RNA phages spontaneously assemble into VLPs upon expression in bacteria such as, for example, *E. coli*. Fusion protein constructs wherein antigenic peptides have been fused to the C-terminus of a truncated form of the A1 protein of Qβ, or inserted within the A1 protein have been described (Kozlovska et al., 1996, *Intervirology* 39: 9-15). Assembly of Qβ particles displaying the fused epitopes typically involves the presence of both the A1 protein-antigen fusion and the wild type coat protein to form a mosaic particle. However, embodiments involving VLPs, and in particular the VLPs of the RNA phage Qβ coat protein, that are exclusively composed of VLP subunits having an antigenic peptide fused thereto, are contemplated.

The production of mosaic particles may be effected in a number of ways. In one exemplary approach, efficient display of the fused epitope on the VLPs is mediated by the expression of the plasmid encoding the Qβ A1 protein fusion having a UGA stop codon between the coat protein and the coat protein extension in an *E. coli* strain harboring a plasmid encoding a cloned UGA suppressor tRNA, which leads to translation of the UGA codon into Trp (pISM3001 plasmid (Smiley et al., 1993, *Gene* 134:33-40). In a second exemplary approach, the coat protein gene stop codon is modified into UAA, and a second plasmid expressing the A1 protein-antigen fusion is co-transformed. The second plasmid encodes a different antibiotic resistance and the origin of replication is compatible with the first plasmid. In a third exemplary approach, Qβ coat protein and the A1 protein-antigen fusion are encoded in a bicistronic manner, operatively linked to a promoter such as the Trp promoter (Kozlovska et al., 1996, *Intervirology* 39:9-15).

Further VLPs suitable for fusion of antigens or antigenic determinants are described in, for example, International Publication No. WO 03/024481 and include bacteriophage fr, RNA phase MS-2, capsid protein of papillomavirus, retrotransposon Ty, yeast and also Retrovirus-like-particles, HIV2 Gag, Cowpea Mosaic Virus, parvovirus VP2 VLP, HBsAg (U.S. Pat. No. 4,722,840, EP0020416B1). Examples of chimeric VLPs suitable for use as the immunogenic carrier include those described in Kozlovska et al., 1996, *Intervirology* 39:9-15. Further examples of VLPs suitable for use as the immunogenic carrier include, but are not limited to, HPV-1, HPV-6, HPV-11, HPV-16, HPV-18, HPV-33, HPV-45, CRPV, COPV, HIV GAG, Tobacco Mosaic Virus, Virus-like particles of SV-40, Polyomavirus, Adenovirus, Herpes Simplex Virus, Rotavirus, and Norwalk virus.

In one particular embodiment, a vaccine construct containing the CSP peptide containing amino acids 5-19 of SEQ ID NO:1 is synthesized by conjugating the peptide to Qβ bacteriophage VLPs using a bifunctional cross-linker (SMPH). The CSP peptide can be modified to include a linker peptide to the C-terminus (e.g., a GGGC linker sequence; SEQ ID NO:2) or the N-terminus (e.g., a CGGG linker sequence; SEQ ID NO:3) to the N-terminus. The SMPH cross-linker conjugates free amines on the surface of the Qβ VLPs to the cysteine residue of the linker peptide. In this synthesis methodology, the Qβ VLP is purified from free, unconjugated crosslinker, and then reacted with the CSP peptide at a molar ratio of about 10 peptide:1 VLP.

For any recombinantly expressed antigenic CSP peptide according to the invention (whether or not coupled to an immunogenic carrier), the nucleic acid that encodes the peptide or protein is also an aspect of the present invention, as is an expression vector comprising the nucleic acid, and a host cell containing the expression vector (autonomously or chromosomally inserted). A method of recombinantly producing the peptide or protein by expressing it in the above host cell and isolating the immunogen therefrom is a further aspect of the invention.

In some embodiments, the antigenic CSP peptide can be chemically coupled to the immunogenic carrier using techniques well known in the art. Conjugation can occur to allow free movement of peptides via single point conjugation (e.g., either N-terminal or C-terminal point) or as a locked down structure where both ends of peptides are conjugated to either an immunogenic carrier protein or to a scaffold structure such as a VLP. Conjugation occurs via conjugation chemistry known to those skilled in the art such as via cysteine residues, lysine residues, or another carboxy moiety. Thus, for example, for direct covalent coupling, it is possible to use a carbodiimide, glutaraldehyde, or N-[γ-maleimidobutyryloxy] succinimide ester, using common commercially available hetero-bifunctional linkers such as 1-cyano-4-dimethylaminopyridinium tetrafluoroborate (CDAP) or succinimidyl 3-(2-pyridyldithio)propionate (SPDP).

Examples of conjugation of peptides, particularly cyclized peptides, to a protein carrier via acylhydrazine peptide derivatives are described in, for example, International Publication No. WO 03/092714. After the coupling reaction, the immunogen can easily be isolated and purified using, for example, a dialysis method, a gel filtration method, a fractionation method, etc. Peptides terminating with a cysteine residue (preferably with a linker outside the cyclized region) may be conveniently conjugated to a carrier protein via maleimide chemistry.

When the immunogenic carrier is a VLP, several antigenic peptides, either having an identical amino acid sequence or a different amino acid sequence, may be coupled to a single VLP particle, leading preferably to a repetitive and ordered structure presenting several antigenic determinants in an oriented manner as described in International Publication Nos. WO 00/32227, WO 03/024481, WO 02/056905 and WO 04/007538. Thus, the antigenic peptide displayed by one VLP subunit in a VLP may the same or different than the antigenic peptide displayed by a second VLP subunit in the same VLP. In other embodiments, one or several antigen molecules can be attached to one VLP subunit. A specific feature of the VLP of the coat protein of RNA phages, and in particular of the Qβ coat protein VLP, is thus the possibility to couple several antigens per subunit. This allows for the generation of a dense antigen array.

Another feature of VLPs derived from RNA phage is their high expression yield in bacteria that allows production of large quantities of material at affordable cost. Moreover, the use of the VLPs as carriers allows the formation of robust antigen arrays and conjugates, respectively, with variable antigen density. In particular, the use of VLPs of RNA phages, and in particular the use of the VLP of RNA phage Qβ coat protein, allows a very high antigen density to be achieved.

The CSP-targeting VLP may be used to treat a subject having, or at risk of having, a condition characterized, at least in part, by cells that express CSP. Such conditions include, but are not limited to, malaria.

As used herein, "treat" or variations thereof refer to reducing, limiting progression, ameliorating, or resolving, to any extent, the symptoms or signs related to a condition. A "sign" or "clinical sign" refers to an objective physical finding relating to a particular condition capable of being found by one other than the patient. A "symptom" refers to any subjective evidence of disease or of a patient's condition.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject. Typically, the CSP-targeted VLP will be used prophylactically to reduce the likelihood that the malaria parasite reaches the liver.

Treatment that is prophylactic—e.g., initiated before a subject manifests a symptom or clinical sign of the condition such as, for example, while a tumor remains subclinical—is referred to herein as treatment of a subject that is "at risk" of having the condition. As used herein, the term "at risk" refers to a subject that may or may not actually possess the described risk. Thus, for example, a subject "at risk" of developing a condition is a subject possessing one or more risk factors associated with the condition such as, for example, genetic predisposition, ancestry, age, sex, geographical location, lifestyle, or medical history. Thus, the CSP-targeted VLP may be administered before a subject manifests a symptom or clinical sign of malaria. In some embodiments, the CSP-targeted VLP may be administered before a subject travels to a geographical location where malaria may be prevalent.

Accordingly, a composition can be administered before, during, or after the subject first exhibits a symptom or clinical sign of the condition (e.g., malaria). Treatment initiated before the subject first exhibits a symptom or clinical sign associated with the condition may result in decreasing the likelihood that the subject experiences clinical evidence of the condition compared to a subject to which the composition is not administered, decreasing the severity of symptoms and/or clinical signs of the condition, and/or completely resolving the condition. Treatment initiated after the subject first exhibits a symptom or clinical sign associated with the condition may result in decreasing the severity of symptoms and/or clinical signs of the condition compared to a subject to which the composition is not administered, and/or completely resolving the condition.

Thus, the method includes administering an effective amount of the composition to a subject having, or at risk of having, a condition characterized, at least in part, by cells that express CSP. In this aspect, an "effective amount" is an amount effective to reduce, limit progression, ameliorate, or resolve, to any extent, a symptom or clinical sign related to the condition.

Thus, the CSP-targeting Qβ VLP described herein may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the CSP-targeting Qβ VLP without causing any undesirable biological effects or interacting in a deleterious manner with any of the other components of the pharmaceutical composition in which it is contained.

The CSP-targeting Qβ VLP may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, a CSP-targeting Qβ VLP may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the CSP-targeting Qβ VLP into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of CSP-targeting Qβ VLP administered can vary depending on various factors including, but not limited to, the cancer being treated, the weight, physical condition, and/or age of the subject, and/or the route of administration. Thus, the absolute weight of CSP-targeting Qβ VLP included in a given unit dosage form can vary widely, and depends upon factors such as the species, age, weight and physical condition of the subject, and/or the method of administration. Accordingly, it is not practical to set forth generally the amount that constitutes an amount of CSP-targeting Qβ VLP effective for all possible applications. Those of ordinary skill in the art, however, can readily determine the appropriate amount with due consideration of such factors.

In some embodiments, the method can include administering sufficient CSP-targeting Qβ VLP to provide a dose of, for example, from about 50 ng/kg to about 1 mg/kg to the subject, although in some embodiments the methods may be performed by administering CSP-targeting Qβ VLP in a dose outside this range.

In some embodiments, the method includes administering sufficient CSP-targeting Qβ VLP to provide a minimum dose of at least 50 ng/kg such as, for example, at least 100 ng/kg, at least 200 ng/kg, at least 300 ng/kg, at least 400 ng/kg, at least 500 ng/kg, at least 600 ng/kg, at least 700 ng/kg, at least 800 ng/kg, at least 900 ng/kg, at least 1 μg/kg, at least 2 μg/kg, at least 5 μg/kg, at least 10 μg/kg, at least 20 μg/kg, at least 50 μg/kg, at least 100 μg/kg, at least 200 μg/kg, or at least 500 μg/kg.

In some embodiments, the method includes administering sufficient CSP-targeting Qβ VLP to provide a maximum dose of no more than 1 mg/kg, no more than 500 μg/kg, no more than 250 μg/kg, no more than 200 μg/kg, no more than 150 μg/kg, no more than 100 μg/kg, no more than 50 μg/kg, no more than 25 μg/kg, no more than 10 μg/kg, no more than 5 μg/kg, no more than 2 μg/kg, no more than 1 μg/kg, no more than 800 ng/kg, no more than 600 ng/kg, no more than 500 ng/kg, no more than 400 ng/kg, no more than 300 ng/kg, no more than 250 ng/kg, no more than 150 ng/kg, no more than 100 ng/kg, no more than 50 ng/kg, or no more than 25 ng/kg.

In some embodiments, the method includes administering sufficient CSP-targeting Qβ VLP to provide a dose that falls within a range having as endpoints any minimum dose listed above and any maximum dose listed above that is greater than the minimum does. For example, in some embodiments, the method can includes administering sufficient CSP-targeting Qβ VLP to provide a dose of from 200 ng/kg to about 10 μg/kg to the subject, for example, a dose of from about 700 ng/kg to about 5 μg/kg. In certain embodiments, the method can include administering sufficient CSP-targeting Qβ VLP to provide a dose that is equal to any minimum dose or any maximum dose listed above. Thus, for example, the method can include administering sufficient CSP-targeting Qβ VLP to provide dose of 200 ng/kg, 700 ng/kg, 1 μg/kg, 5 μg/kg, 10 μg/kg, etc.

In some embodiments, a dose of CSP-targeting Qβ VLP may be administered, for example, from a single administration to multiple administrations per week, although in some embodiments the method can be performed by administering CSP-targeting Qβ VLP at a frequency outside this range. When multiple administrations are used within a certain period, the amount of each administration may be the same or different. For example, a dose of 1 mg per day may be administered as a single administration of 1 mg, two administrations of 0.5 mg, or as a first administration of 0.75 mg followed by a second administration of 0.25 mg. Also, when multiple administrations are used within a certain period, the interval between administrations may be the same or be different.

In certain embodiments, CSP-targeting Qβ VLP may be administered at minimum frequency of at least once per year such as, for example, at least once every six months, at least once every four months, at least once every three months, at least once every two months, at least once per month, or at least once every two weeks.

In certain embodiments, CSP-targeting Qβ VLP may be administered at maximum frequency of no more than once per week such as, for example, no more than once every two weeks, no more than once per month, no more than once every two months, no more than once every three months, no more than once every six months, or once per year.

In some embodiments, CSP-targeting Qβ VLP may be administered at a frequency defined by a range having as endpoints any minimum frequency listed above and any maximum frequency listed above that is more frequent than the minimum frequency.

The duration of administration of an antigenic CSP peptide according to the invention, e.g., the period of time over which an antigenic CSP peptide is administered, can vary, depending on any of a variety of factors, e.g., patient response, etc. For example, an antigenic CSP peptide can be administered over a period of time ranging from about one day to about one week, from about two weeks to about four weeks, from about one month to about two months, from about two months to about four months, from about four months to about six months, from about six months to about eight months, from about eight months to about one year, from about one year to about two years, or from about two years to about four years, or more. In some embodiments, the CSP-targeting Qβ VLP may be administered as a once off treatment. In other embodiments, the CSP-targeting Qβ VLP may be administered for the life of the subject. In certain embodiments, the CSP-targeting Qβ VLP may be administered may be administered monthly (or every four weeks) until effective.

In some cases, the CSP-targeting Qβ VLP may be administered at an initial frequency for an initial period and then administered at a lower frequency thereafter. For example, a dosing regimen may include administering three doses of the CSP-targeting Qβ VLP at a frequency of once per month (i.e., an initial dose followed by a second dose one month after the initial dose) followed by an additional dose six months after the initial dose.

When a CSP-targeting Qβ VLP composition is used for prophylactic treatment, it may be generally administered for priming and/or boosting doses. Boosting doses, when administered, are adequately spaced (e.g., yearly) to boost the level of circulating antibody that has fallen below a desired level. Boosting doses may include a CSP-targeting peptide either with or in the absence of the original immunogenic carrier. A booster composition may include an alternative immunogenic carrier or may be in the absence of any carrier. Moreover, a booster composition may be formulated either with or without adjuvant.

In some cases, the method can further include administering to the subject an additional therapeutic agent effective for treating the condition (e.g., malaria). For example, therapy involving the CSP-targeting Qβ VLP may be combined with conventional therapies for malaria.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Production and Characterization of CIS43 Epitope Displaying Bacteriophage Qβ VLPs Qβ bacteriophage VLPs were prepared were produced in *E. coli* using methods previously described for the production of bacteriophage PP7 VLPs (Tumban et al., 2011. *PLoS One* 6(8):e23310; PMID: 21858066). The fifteen amino acid CIS43 epitope peptide was synthesized (GenScript Biotech Corp., Piscataway, NJ) and modified to contain a C-terminal GLY-GLY-GLY-CYS (SEQ ID NO:2) linker sequence (NPDPNANPNVDPNANGGGC, SEQ ID NO:4). The peptide was conjugated directly to surface lysines on Qβ bacteriophage VLPs using the bidirectional crosslinker succinimidyl 6-[(beta-maleimidopropionamido) hexanoate] (SMPH; Thermo Fisher Scientific, Inc., Waltham, MA) as previously described (Tumban et al., 2011. *PLoS One* 6(8): e23310; PMID: 21858066). The efficiency of conjugation was assessed by gel electrophoresis using a 10% SDS denaturing polyacrylamide gel. Briefly, peptide conjugation results in a mobility shift of the Qβ coat protein due to an increase in molecular weight. The percentage of coat protein with zero, one, two, or more attached peptides was determined using ImageJ software (Schneider, et al., 2012. *Nature Methods* 9:671-675).

Presence of the CIS43 peptide on VLPs was confirmed by ELISA. Briefly, 250 ng of VLPs were used to coat wells of an ELISA plate. Wells were probed with dilutions of mAb CIS43 (Kisalu et al., 2018, *Nat Med* 24:408-416), followed by a 1:4000 dilution of horseradish peroxidase (HRP)-labeled goat anti-human IgG (Jackson ImmunoResearch Laboratories, Inc., West Grove, PA). The reaction was developed using 3,3',5,5'-tetramethylbenzidine (TMB) substrate (Thermo Fisher Scientific Inc., Waltham, MA) and stopped using 1% HCl. Reactivity of the CIS43 mAb for the CIS43 VLPs was determined by measuring optical density at 450 nm ($OD_{450}$) using a plate reader (ACCUSKAN, Fisher Scientific). With the exception of preliminary murine immunogenicity studies, all CIS43 VLPs and WT Qβ VLPs were LPS-depleted by three rounds of phase separation using Triton X-114 (Sigma-Aldrich, St. Louis, MO), as previously described (Aida et al., 1990. *J Immunol Methods* 132(2): 191-195).

Mouse Immunization Studies

Groups of four-week old female Balb/c mice (Jackson Laboratory, Bar Harbor, ME) were immunized intramuscularly with 5 µg of CIS43 VLPs or control (unmodified) Qβ VLPs. Mice were typically boosted twice after the initial prime, at three-week or four-week intervals. Some vaccinations were performed using proprietary ADVAX adjuvants provided by Vaxine Pty Ltd (Adelaide, Australia). In these experiments, mice were intramuscularly immunized with 5 µg VLPs in combination with 20 µl the following: ADVAX, ADVAX-2, ADVAX-3, ADVAX-4, ADVAX-5, or synthetic oligonucleotide adjuvant CpG55.2. An additional group of mice received 5 µg of unadjuvanted CIS43 VLPs. In these experiments, mice were boosted four weeks after the prime and selected groups received a second boost at three months. In each mouse experiment, serum samples were collected prior to each boost and, in some cases, at additional later timepoints following the final boost.

Cynomolgus Monkey Immunization Studies

Groups (n=3/group) of male and female cynomolgus monkeys (*Macaca fascicularis*) of varying ages (2 years to 17 years) and varying body weights (2.58 kg to 13.30 kg) were immunized with 100 µg of unadjuvanted CIS43 VLPs, or the same dose in combination with 0.5 mg of ADVAX-3. One month after the prime, animals were boosted with 50 µg of VLPs with or without ADVAX-3. A negative control group received similar doses of unmodified Qβ VLPs. Serum was collected at the initial immunization and at two-week intervals thereafter.

Quantitating Antibody Responses

Serum antibodies against rPfCSP were detected by ELISA. Wells of IMMULON 2 plates (Thermo Fisher Scientific, Inc., Waltham, MA) were coated with 250 ng of rPfCSP in 50 µl PBS and incubated at 4° C. overnight. rPfCSP (referred to as CSP in our studies) used in these studies was recombinantly expressed in *Pseudomonas fluorescens* as previously described (Noe et al., 2014. *PLoS One* 9(9):e107764). Following incubation, wells were blocked with PBS-0.5% milk for two hours at room temperature. Sera isolated from immunized animals were serially diluted in PBS-0.5% milk and applied to wells and incubated at room temperature for 2.5 hours. Dilution of 1:4000 of HRP-labeled goat anti-mouse IgG (or, for macaque sera, a 1:4000 dilution of HRP-labeled goat anti-human IgG) was used to detect reactivity to target antigen. Reactivity was determined using TMB substrate as described above. Endpoint dilution titer was defined as the greatest sera dilution that yielded an $OD_{450}$ greater than two-fold over background. For mouse sera, anti-CSP antibody concentrations were quantitated by ELISA by using a standard curve using known concentrations of the anti-CSP mouse mAb 2A10 (Anker et al., 1990. *Eur J Immunol.* 20(12):2757-2761).

For peptide ELISAs, wells of IMMULON 2 plates (Thermo Fisher Scientific, Inc., Waltham, MA) were coated with 500 ng streptavidin (Invitrogen, Carlsbad, CA) for two hours at 37° C. Following washing, the bidirectional cross-linker succinimidyl 6-[(beta-maleimidopropionamido) hexanoate] (SMPH; Thermo Fisher Scientific, Inc., Waltham, MA) was added to wells at 1 µg/well and incubated for two hours at room temperature. Specific peptides were added to the wells at 1 µg/well and incubated overnight at 4° C. Wells were then incubated with dilutions of mouse sera and binding was detected as described above.

Measurement of Antibody Avidity

The avidity index (AI) of anti-CSP antibodies was evaluated using a ELISA-based chaotrope avidity assay (Fialová et al., 2017. *J Clin Lab Anal.* 31(6):1-9). This protocol followed our standard ELISA (described above), except that following the serum incubation, wells were treated with 6M urea for 10 minutes. The AI was calculated as the ratio of the ELISA absorbance value of 6M urea-treated wells ($A_{6M\ UREA}$) to control wells treated with PBS ($A_c$); $AI=A_{6MUREA}/A_c$. Multiple dilutions of sera were analyzed and all samples were tested in duplicate.

Mouse Pb-PfCSP Sporozoite Challenge

Challenge studies were performed using female 6-8 week old C57BL/6 mice. Mice (n=7/group) were immunized intramuscularly with 5 µg of CIS43 VLPs with or without adjuvant three times at three-week intervals. Separate control groups were immunized with unmodified Qβ VLPs, PBS, or adjuvant alone. Each immunogen was blinded to minimize the potential for bias in animal handling during the challenge portion of the study. Serum was collected following the third immunization.

Mice were challenged using transgenic *P. berghei* sporozoites engineered to express luciferase and full-length *P. falciparum* CSP in place of *P. berghei* CSP (denoted as Pb-Pf-Luc). Mice were challenged directly using sporozoites or by using infected mosquitoes. For the sporozoite challenge, Pb-Pf-Luc sporozoites were freshly harvested from female *Anopheles stephensi* salivary glands. 1000 sporozoites in 200 µl HBSS/2% FCS were intravenously injected into immunized and naïve mice. 42 hours post challenge, mice were intraperitoneally injected with 100 µl D-luciferin (30 mg/ml) and anesthetized. Liver luminescence was assessed by IVIS Spectrum Imaging System (Perkin Elmer, Inc., Waltham, MA). For mosquito challenges, *A. stephensi* mosquitos were infected by blood feeding on Pb-Pf-Luc-infected mice. Prior to challenge, mice were anesthetized with 2% 2,2,2-tribromoethanol, and then exposed to five mosquitos for a blood meal. Following feeding, mosquitos positive for a blood meal were counted. Liver luminescence was assessed 42 hours post challenge, as described above. Four days later, blood smears were taken from mice to evaluate parasitemia.

Passive Transfer Study

Cynomolgus monkey sera was pooled within each group, heat inactivated for 30 minutes at 56° C., and filtered through a 0.45 micron filter to remove aggregates. 500 µl of sera was then passively transferred into each mouse (n=4-5 mice/group) via intravenous tail injection. 500 µl of PBS was intravenous injected into the negative control group. Two hours following serum transfer, mice were challenged by *A. stephensi* mosquito bite, as described above. Liver luminescence was evaluated 42 hours post challenge, and parasitemia was evaluated by blood smears four days later, as described above.

Statistics

All statistical analyses of data were performed using PRISM8 software (GraphPad Software, Inc., San Diego, CA).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

```
Sequence Listing Free Text
CSP peptide
                                       SEQ ID NO: 1
PADGNPDPNANPNVDPNAN linker peptide
                                       SEQ ID NO: 2
GGGC linker peptide
                                       SEQ ID NO: 3
CGGG CSP peptide with linker
                                       SEQ ID NO: 4
NPDPNANPNVDPNANGGGC MGG4-15mer:
                                       SEQ ID NO: 5
KQPADGNPDPNANPN MGG4-19mer:
                                       SEQ ID NO: 6
KQPADGNPDPNANPNVDPN

CSP 5D5:
                                       SEQ ID NO: 7
EDNEKLRKPKHKKLK

CSP central repeat peptide:
                                       SEQ ID NO: 8
NANPNANPNANPNANPNA Mal:
                                       SEQ ID NO: 9
NANPNVDPNANPNANPNANP
```

---

What is claimed is:

1. An immunogen comprising:
    an immunogenic carrier comprising a Qβ bacteriophage virus-like particle (VLP); and
    an antigenic malaria circumsporozoite protein (CSP) junction region peptide comprising NPDPNANPNVDPNAN (amino acids 5-19 of SEQ ID NO:1) linked to the immunogenic carrier.

2. The immunogen of claim 1, wherein the immunogenic carrier is linked to the CSP peptide through a succinimidyl-6-[β-maleimidopropionamido]hexanoate (SMPH) cross-linker molecule.

3. The immunogen of claim 1, further comprising a second antigenic CSP peptide linked to the immunogenic carrier.

4. The immunogen of claim 3, wherein the second antigenic CSP peptide comprises the amino acid sequence of SEQ ID NO:5, SEQ ID NO:6, SEQ ID NO:7, SEQ ID NO:8, or SEQ ID NO:9.

5. A composition comprising the immunogen of claim 1.

6. An immunogenic composition comprising:
    the immunogen of claim 1; and
    at least one adjuvant.

7. The immunogenic composition of claim 6, wherein the adjuvant comprises a delta inulin polysaccharide.

8. A method of treating malaria in an individual, the method comprising administering a therapeutically effective amount of an immunogen to the individual, the immunogen comprising:
    an immunogenic carrier comprising a Qβ bacteriophage virus-like particle (VLP); and
    an antigenic malaria circumsporozoite protein (CSP) junction region peptide comprising NPDPNANPNVDPNAN (amino acids 5-19 of SEQ ID NO:1) linked to the immunogenic carrier.

9. The method of claim 8, wherein the immunogen further comprises a second antigenic CSP peptide linked to the immunogenic carrier.

10. The method of claim 9, wherein the second antigenic CSP peptide comprises the amino acid sequence of SEQ ID NO:5, SEQ ID NO:6, SEQ ID NO:7, SEQ ID NO:8, or SEQ ID NO:9.

11. The method of claim 8, wherein the method further comprises administering to the individual at least one additional prophylactic agent for treating malaria.

12. The method of claim 8, wherein the method further comprises administering to the individual at least one additional therapeutic agent for treating malaria.

* * * * *

SEQUENCE LISTING

```
<160> NUMBER OF SEQ ID NOS: 9

<210> SEQ ID NO 1
<211> LENGTH: 19
<212> TYPE: PRT
<213> ORGANISM: Artificial
<220> FEATURE:
<223> OTHER INFORMATION: Circumsporozoite protein (CSP) peptide

<400> SEQUENCE: 1

Pro Ala Asp Gly Asn Pro Asp Pro Asn Ala Asn Pro Asn Val Asp Pro
1               5                   10                  15

Asn Ala Asn

<210> SEQ ID NO 2
<211> LENGTH: 4
<212> TYPE: PRT
<213> ORGANISM: Artificial
<220> FEATURE:
```

```
<223> OTHER INFORMATION: Linker peptide

<400> SEQUENCE: 2

Gly Gly Gly Cys
1

<210> SEQ ID NO 3
<211> LENGTH: 4
<212> TYPE: PRT
<213> ORGANISM: Artificial
<220> FEATURE:
<223> OTHER INFORMATION: Linker peptide

<400> SEQUENCE: 3

Cys Gly Gly Gly
1

<210> SEQ ID NO 4
<211> LENGTH: 19
<212> TYPE: PRT
<213> ORGANISM: Artificial
<220> FEATURE:
<223> OTHER INFORMATION: Circumsporozoite protein (CSP) peptide with
      linker

<400> SEQUENCE: 4

Asn Pro Asp Pro Asn Ala Asn Pro Asn Val Asp Pro Asn Ala Asn Gly
1               5                   10                  15

Gly Gly Cys

<210> SEQ ID NO 5
<211> LENGTH: 15
<212> TYPE: PRT
<213> ORGANISM: Artificial
<220> FEATURE:
<223> OTHER INFORMATION: MGG4 15mer peptide

<400> SEQUENCE: 5

Lys Gln Pro Ala Asp Gly Asn Pro Asp Pro Asn Ala Asn Pro Asn
1               5                   10                  15

<210> SEQ ID NO 6
<211> LENGTH: 19
<212> TYPE: PRT
<213> ORGANISM: Artificial
<220> FEATURE:
<223> OTHER INFORMATION: MGG4 19mer peptide

<400> SEQUENCE: 6

Lys Gln Pro Ala Asp Gly Asn Pro Asp Pro Asn Ala Asn Pro Asn Val
1               5                   10                  15

Asp Pro Asn

<210> SEQ ID NO 7
<211> LENGTH: 15
<212> TYPE: PRT
<213> ORGANISM: Artificial
<220> FEATURE:
<223> OTHER INFORMATION: Circumsporozoite protein (CSP) 5D5 peptide

<400> SEQUENCE: 7

Glu Asp Asn Glu Lys Leu Arg Lys Pro Lys His Lys Lys Leu Lys
1               5                   10                  15

<210> SEQ ID NO 8
```

```
<211> LENGTH: 18
<212> TYPE: PRT
<213> ORGANISM: Artificial
<220> FEATURE:
<223> OTHER INFORMATION: Circumsporozoite protein (CSP) central repeat
      peptide

<400> SEQUENCE: 8

Asn Ala Asn Pro Asn Ala Asn Pro Asn Ala Asn Pro Asn Ala Asn Pro
1               5                   10                  15

Asn Ala

<210> SEQ ID NO 9
<211> LENGTH: 20
<212> TYPE: PRT
<213> ORGANISM: Artificial
<220> FEATURE:
<223> OTHER INFORMATION: Mal peptide

<400> SEQUENCE: 9

Asn Ala Asn Pro Asn Val Asp Pro Asn Ala Asn Pro Asn Ala Asn Pro
1               5                   10                  15

Asn Ala Asn Pro
            20
```